April 26, 1960 E. G. FISHER Plant Pat. 1,937
ROSE PLANT
Filed July 22, 1959
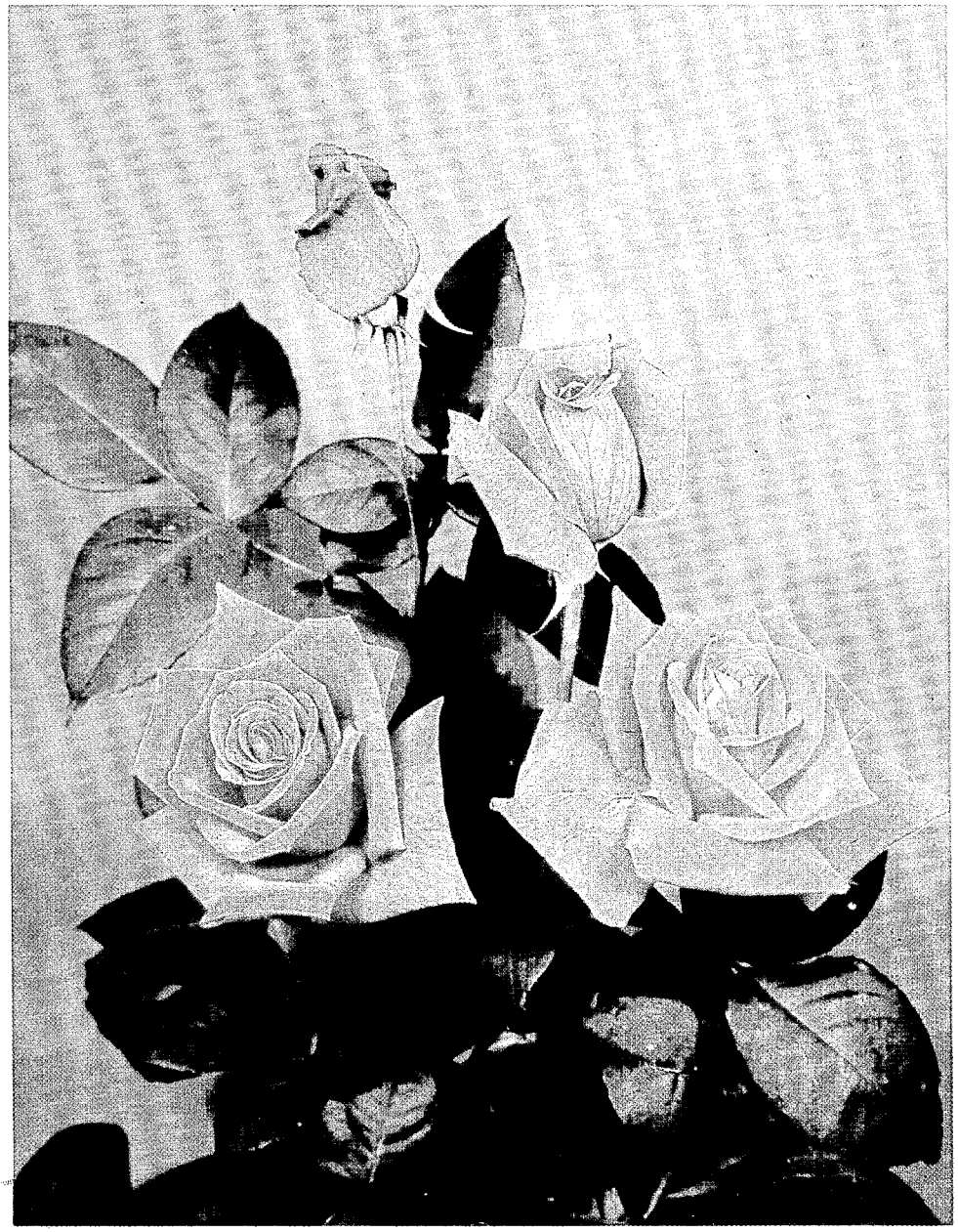
INVENTOR
Esther Gladys Fisher
BY Robb & Robb
ATTORNEYS United States Patent Office Plant Pat. 1,937
Patented Apr. 26, 1960

1,937

ROSE PLANT

Esther Gladys Fisher, Woburn, Mass., assignor to Arnold-Fisher Company, Middlesex, Mass., a corporation of Massachusetts Application July 22, 1959, Serial No. 828,922

1 Claim. (Cl. 47—61)

The present invention relates to a new and distinct variety of rose plant of the hybrid tea class, which was originated by me by crossing two unnamed and unpatented red rose seedlings formerly bred by me.

The primary objective of this breeding was to produce a new rose variety in which there is combined the best characteristics of the parent varieties, and more particularly, which is useful for growing in the greenhouse for the florist trade. In achieving this objective, I used in making the cross aforementioned a female parent which had a bloom of great color beauty and form, but which was of such size that the stem and neck would not properly support the bloom. The male parent chosen was characterized by having a long and strong stem and neck, but the bloom thereof though large and attractive, was more of a rose red color and not a true red. The resulting seedling of these parents achieved the following unique combination of characteristics which not only distinguish the same from the parents, but also from all other varieties of which I am aware:

(1) Long and strong flower stems, thereby making the new variety especially suitable for cut flowers which are usually priced according to the length of the stems;

(2) A habit of blooming as well in the winter as in the summer, this being another important improvement in a cut flower type of rose by virtue of the fact that higher prices usually prevail in the winter season;

(3) Flower buds of long and high-centered form, especially suitable for the florist trade;

(4) A distinctive Currant Red general color tonality of both the buds and open flowers; and (5) Long-lasting flower qualities.

My new variety more clearly resembles the variety known as "Happiness" (Plant Patent No. 911) than any other variety heretofore available in commerce, but the flowers of "Happiness" are darker red in color and tend to turn blue or lavender-tinged with age, whereas the flowers of my new variety remain a clear non-bluing red. Also, the variety "Happiness" produces very few blooms during the cold winter months, whereas my new variety blooms as well during the winter as during the summer.

Asexual reproduction of my new variety by both grafting and budding, as performed by me in both the greenhouse and outdoors at Woburn, Massachusetts, shows that the aforementioned characteristics and distinctions come true to form and are established and transmitted through succeeding propagations.

The accompanying drawing shows typical specimens of the flowers and foliage of my new variety in different stages of development and as depicted in color as nearly true as it is resonably possible to make the same in a color illustration of this character.

The following is a detailed description of my new variety, with color terminology in accordance with the Horticultural Colour Chart of the Royal Horticultural Society (hereinafter abbreviated as "HCC"), and Nickerson Color Fan, published by Munsell Color Company, Incorporated (hereinafter abbreviated as "Nickerson"), as indicated, except where general color terms of ordinary dictionary significance are obvious:

(Observations made from specimens grown at Woburn, Massachusetts, with the bud and open flower specimens being observed in a greenhouse during the month of June.)

Type: Seedling; greenhouse and outdoor; for cut flowers and for garden decoration.

Class: Hybrid tea.

Propagation: Holds its distinguishing characteristics through succeeding propagations by both budding and grafting.

*Plant*

Growth habit: Strong and fast grower; usually attains height of about 6 feet; although primarily a greenhouse rose, it also grows well outdoors.

Blooming habit: Blooms freely throughout the year in the greenhouse.

Stem: Long (from 20 inches to 48 inches); strong. Color—Sage Green, Plate 000861, vol. 2 (HCC).

Thorns: Moderate number; varies from 10 to 30 on stems 2 feet in length; largest thorns measure about ¼ inch in length; slant downwards. Color: base—Strong Purplish Red, Hue 10RP-4/12 (Nickerson); tip—Moderate Yellow Green, Hue 2.56Y-5/5.

Foliage:

*Type.*—Pinnately compound of 3 to 7 leaflets, but normally 5.

*Color.*—Upper surface—Greyish Olive Green, Hue 5GY-3/2 (Nickerson), with edges sometimes tinted Erythrite Red, Plate 0027/2, vol. 1 (HCC) which is noticeable around the serrations, and sometimes a few leaves have a faint suggestion of Erythrite Red, Plate 0027/2, vol. 1 (HCC) tinting the leaf. Under surface—Sage Green, Plate 000861/1, vol. 1 (HCC), with shading of Erythrite Red, Plate 0027/2, vol. 1 (HCC) on some leaves.

*Quantity.*—Abundant.

*Size.*—Large; terminal leaflets average approximately 3 inches long and 2 inches wide.

*Shape.*—Broad oval, with rounded base; leaflets have accuminate apex, with edges moderately serrated.

*Texture.*—Leathery; firm.

*Rachis.*—Strong; grooved. Color.—under side—Moderate Yellow Green, Hue 2/56Y-5/5 (Nickerson); upper side—Moderate Olive Green, Hue 2/56Y-4/3 (Nickerson), with touch of Erythrite Red, Plate 0027/2, vol. 1 (HCC) at times.

*Stipules.*—From ½ inch to ⅝ inch long; with points varied. Color.—Spinach Green, Plate 0960/1, vol. 2 (HCC), with tips sometimes Erythrite Red, Plate 0027/2, vol. 1 (HCC).

*Flower*

Bud:

*Size.*—Large; from 2 inches to 2½ inches long.

*Form.*—Long and high-centered.

*Color.*—Currant Red, Plate 821/1, vol. 1 (HCC).

*Sepals.*—From 1 to 1½ inches long; slightly foliaceous at times and folding back on stem; approximately ⅜ inch wide at bud. Color.—Pod Green, Plate 061/1, vol. 2 (HCC) where it joins corolla, with outer surface Fern Green, Plate 0862/1, vol. 2 (HCC), and with tip Willow Green, Plate 000862/1, vol. 2 (HCC).

*Calyx (ovary).*—Fairly small and smooth. Color.—Moderate Yellow Green, Hue 2.56Y-5/6 (Nickerson).

*Peduncle.*—Strong; slightly rough to touch; no predominating thorns; about 4 inches long. Color.—

Moderate Yellow Green, Hue 2.56Y-5/5 (Nickerson).

Bloom:

*Borne.*—Singly; on long stems.

*Size (when fully open).*—From 5½ inches to 6½ inches.

*Form.*—High-centered; opens to a wide spreading flower which shows stamens in its last stages.

*Petalage.*—Average from 25 to 35 petals.

*Scent.*—Moderate and pleasing fragrance.

*Longevity.*—Long-lasting.

Petals:

*Texture.*—Moderately heavy; velvety.

*Shape.*—Approximately round, but petals reflex with age and in so doing, form about three points.

*Color.*—Inside of petal—Currant Red, Plate 821/1, vol. 1 (HCC). Outside of petal—slightly lighter than Currant Red, Plate 821/1, vol. 1 (HCC), with a tiny touch of yellow where petal joins calyx.

*Reproductive organs*

Stamens: Prominent red filaments curving inwardly, with outer filaments approximately ½ inch long, but slightly shorter near pistil; anthers good size and about ⅛ inch long.

Pistil: Color.—red styles tipped with yellow and with minute light colored flecks showing on styles.

I claim:

A new and distinct variety of rose plant of the hybrid tea class, substantially as herein shown and described, characterized particularly as to novelty by the unique combination of long and strong flower stems, a habit of blooming as well in the winter as in the summer, a long and high-centered bud form, a distinctive Currant Red general color tonality of both the buds and open flowers, and long-lasting qualities of the flowers.

No references cited.